Jan. 24, 1933. A. E. HENNINGER Plant Pat. 53
COLORED SEEDLESS GRAPEFRUIT
Filed Jan, 6, 1932
Fig I.
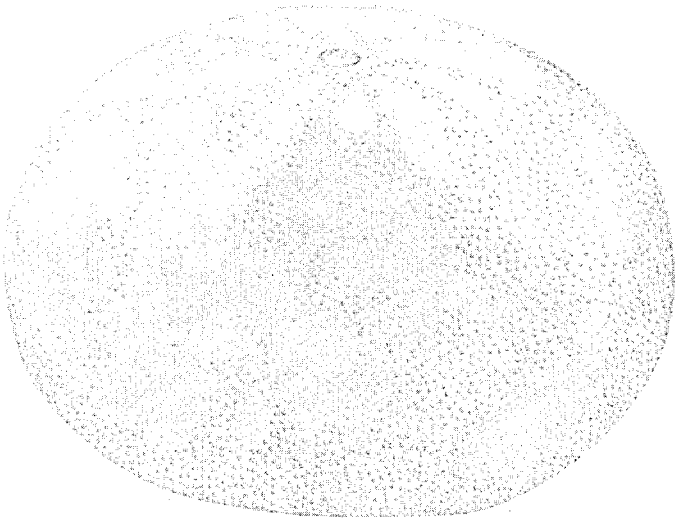
Fig II
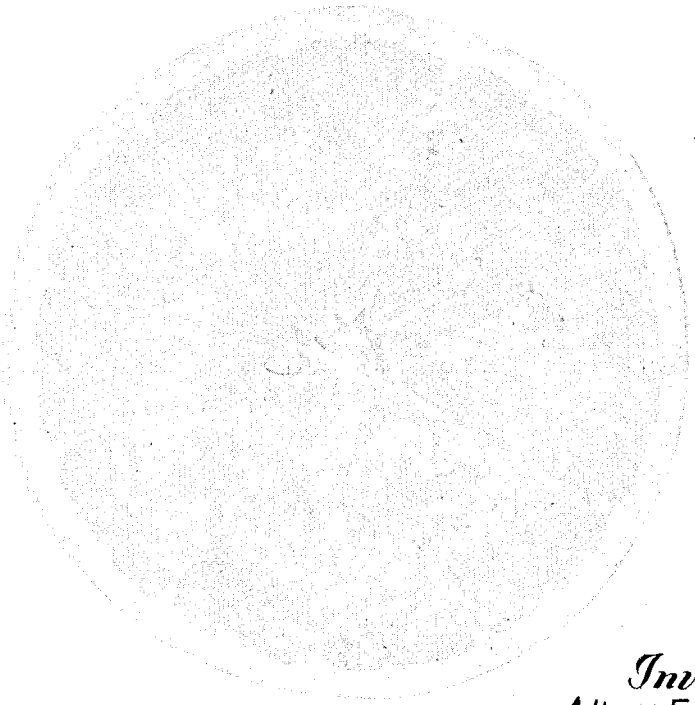
Inventor:
Albert E. Henninger,
By Lester L. Sargent
Attorney
Drawings by Ruby Hills Patented Jan. 24, 1933

Plant Pat. 53

UNITED STATES PATENT OFFICE

ALBERT E. HENNINGER, OF McALLEN, TEXAS

COLORED SEEDLESS GRAPE FRUIT

Application filed January 6, 1932. Serial No. 585,079.

The object of my invention is the production of a new type of seedless grape fruit, pink to red colored rind showing pink tint thru the rind, red flesh deepening to a ruby red border where pulp and rind contact. The fruit is illustrated in the accompanying drawing, in which—

Figure 1 is a perspective view of the fruit; and

Figure 2 is a section thru the center of the fruit.

On March 30th, 1929, a fruit was gathered which showed a colored rind as well as a red colored flesh. The tree from which it was picked is a Thompson pink grape fruit purchased from Reasoner Brothers' Royal Palm Nurseries, Oneco, Florida and planted in the spring of 1926. The Thompson pink was developed from a "bud sport" found on a Marsh seedless tree on the W. B. Thompson farm near Oneco, Florida. Marsh seedless and Thompson pink fruit are described in detail in "The Cultivation of Citrus Fruits" by H. Harold Hume, pages 102–103, 1928 edition.

In August 1929, I found a fruit which had been knocked off the tree by men cultivating the orchard. Half buried in soil it showed a prominent blush. In the fall of 1929, four more fruit were discovered on this limb, one of which was exhibited at the Valley Fair at Harlingen, Texas in Nov. 1929, with card identifying the fruit but not the grower.

This season 1931, there are 20 fruit on this limb and one fruit on a young tree budded from this limb, which is also showing a colored rind like the parent limb.

The freeze of Jan. 1930 froze the limb back so severely, no fruit set on it, season of '30–31.

My observation of this fruit indicates that it

1st. Has a deeper colored flesh than the Thompson pink seedless grapefruit, with a border ruby red.

2nd. The rind is colored similar to a Foster pink.

3rd. Appears to hold its color longer on the tree and in storage, fading less than does the Thompson or Foster.

4th. Has fewer sections, varying 11 to 12 sections, with an occasional one of 13, usually found in Marsh type. Flesh fine grained.

No stock budded from this limb has been exhibited or sold. At this time, I have 1400 or more trees in the nursery that will caliper three fourths to 1 inch in size besides some 15,000 budded at various times during past season. Preparing to bud about 7500 more immediately.

What I claim is:—

A colored seedless grape fruit as shown and described, characterized by a deep pink almost ruby red color of the flesh, and an external pink rind blush, the fruit having few or no seeds.

ALBERT E. HENNINGER.